United States Patent [19]

Daignault, Jr. et al.

[11] Patent Number: 5,009,655
[45] Date of Patent: Apr. 23, 1991

[54] HOT TIP DEVICE WITH OPTICAL DIAGNOSTIC CAPABILITY

[75] Inventors: Kenneth J. Daignault, Jr., Jefferson; Edward I. McNamara, Chelmsford; Edward L. Sinofsky, Peabody, all of Mass.

[73] Assignee: C. R. Bard, Inc., Murray Hill, N.J.

[21] Appl. No.: 356,437

[22] Filed: May 24, 1989

[51] Int. Cl.⁵ .............................................. A61B 5/06
[52] U.S. Cl. .................................. 606/007; 606/010; 606/015; 606/016; 606/017; 128/395; 128/397
[58] Field of Search ............ 128/303.1, 395, 397–399; 606/2, 3, 7, 10–19, 27, 28; 219/121.6, 121.65, 121.66, 121.85

[56] References Cited

U.S. PATENT DOCUMENTS

| 4,233,493 | 11/1980 | Nath ...................... 219/354 |
| 4,279,246 | 7/1981 | Chikama ...................... 128/6 |
| 4,539,987 | 9/1985 | Nath et al. ...................... 128/303.1 |
| 4,545,390 | 10/1985 | Leary ...................... 128/772 |
| 4,641,650 | 2/1987 | Mok ...................... 128/303.1 |
| 4,646,737 | 3/1987 | Hussein et al. ...................... 128/303.1 |
| 4,654,024 | 3/1987 | Crittenden et al. ...................... 604/49 |
| 4,662,368 | 5/1987 | Hussein et al. ...................... 128/303.1 |
| 4,718,417 | 1/1988 | Kittrell et al. ...................... 128/303.1 |
| 4,730,902 | 3/1988 | Suzuki et al. ...................... 350/311 |
| 4,760,845 | 8/1988 | Kovalcheck ...................... 128/303.1 |
| 4,773,413 | 9/1988 | Hussein et al. ...................... 128/303.1 |
| 4,785,806 | 11/1988 | Deckelbaum ...................... 128/303.1 |
| 4,832,023 | 5/1989 | Murphy-Chutorian ............ 128/398 |

FOREIGN PATENT DOCUMENTS 2826383 12/1979 Fed. Rep. of Germany .
8202604 8/1982 PCT Int'l Appl. .

*Primary Examiner*—Stephen C. Pellegrino
*Assistant Examiner*—David Shay
*Attorney, Agent, or Firm*—Wolf, Greenfield & Sacks

[57] ABSTRACT

A hot tip device, typically used for melting and plowing through stenotic deposits in a coronary artery, is provided with optical diagnostic capabilities. The device includes an elongated, flexible member, a filter glass heating element attached to the distal end of the flexible member and an optical fiber extending through the flexible member and optically coupled to the heating element. The filter glass heating element absorbs a first range of wavelengths for heating and passes a second range of wavelengths for irradiating the artery through the filter glass heating element. In a preferred embodiment, the flexible member is a steerable guidewire, and the filter glass heating element is heated by infrared radiation. Ultraviolet or visible radiation is used to stimulate fluorescence from deposits in the artery.

27 Claims, 2 Drawing Sheets

HOT TIP DEVICE WITH OPTICAL DIAGNOSTIC CAPABILITY

FIELD OF THE INVENTION

This invention relates to a hot tip device that is used in transluminal coronary angioplasty and, more particularly, to a hot tip device having a heating element fabricated of optical filter glass to permit laser heating of the element at one wavelength and laser irradiation through the element at other wavelengths for diagnostic purposes.

BACKGROUND OF THE INVENTION

Transluminal coronary angioplasty involves the non-surgical widening of a passage through an artery that has been narrowed or stenosed by deposits of plaque or plaque-ridden tissue. One approach to coronary angioplasty involves the use of a "hot tip" device which includes a heating element at the distal end of a catheter. The heating element is heated to a temperature of several hundred degrees Centigrade and is moved through a blocked artery to soften and plow through the stenotic material. Due to the high temperatures involved, the hot tip device is kept moving through the artery when it is energized to avoid overheating and burning of tissue.

The heating element in prior art hot tip devices has been metal, and electrical, catalytic and laser heating of the element are known. In the laser-energized hot tip, an optical fiber extends through the catheter and terminates in the heating element. Laser energized hot tip devices are disclosed in German Patent No. 2,826,383 published Dec. 20, 1979, U.S. Pat. No. 4,646,737 issued March 3, 1987 to Hussein et al, U.S. Pat. No. 4,662,368 issued May 5, 1987 to Hussein et al and U.S. Pat. No. 4,773,413 issued Sep. 27, 1988 to Hussein et al. In the disclosed devices, laser energy carried through the optical fiber raises the temperature of the heating element. U.S. Pat. Nos. 4,662,368 and 4,773,413 disclose a lens or window positioned in a cavity in the metal heating element. The window is made of an optically transparent material, such as quartz or sapphire. A portion of the laser energy incident on the window heats the surrounding metal, and a portion of the laser energy passes through the window to assist in heating and vaporizing the plaque.

Techniques have been proposed for distinguishing between plaque and normal tissue by stimulating fluorescence from tissue in an artery and analyzing the characteristics of the fluorescence. U.S. Pat. No. 4,785,806 issued Nov. 22, 1988 to Deckelbaum discloses the use of ultraviolet laser energy for stimulating fluorescence. Fluorescence intensity at selected wavelengths in the blue-green wavelength range is analyzed to distinguish between plaque and normal tissue. The use of a dye to enhance the contrast between the fluorescence from plaque and the fluorescence from normal tissue is disclosed in U.S. Pat. No. 4,641,650 issued Feb. 10, 1987 to Mok. The use of visible light to stimulate fluorescence from artherosclerotic plaque is disclosed in U.S. Pat. No. 4,718,417 issued Jan. 12, 1988 to Kittrell et al.

The ability to distinguish between plaque and normal tissue enables the surgeon to better control the angioplasty procedure. It is desirable to provide such diagnostic capability in hot tip devices. In the past, the heating element usually blocked the distal end of the optical fiber in hot tip devices, and optical diagnostic procedures have not been feasible.

Because of the requirement for accessing blood vessels of very small diameter, it has become commonplace in transluminal coronary angioplasty to use guidewires for controlling the placement of catheters. Catheters of sufficiently small diameter to be used in a small blood vessel typically lack the torsional rigidity to be adequately controlled as they are advanced through the vascular system to the obstructed site. Guidewires have an extremely small diameter, flexibility and sufficient torsional rigidity to be advanced to very small diameter blood vessels. The catheter is then advanced over the guidewire to the obstructed site. A steerable guidewire suitable for use in a balloon dilatation procedure is disclosed in U.S. Pat. No. 4,545,390 issued Oct. 8, 1985 to Leary and assigned to assignee of the present application.

It is a general object of the present invention to provide an improved hot tip device for coronary angioplasty.

It is another object of the present invention to provide a hot tip device having optical diagnostic capability.

It is a further object of the present invention to provide improved methods for coronary angioplasty.

It is yet another object of the present invention to provide a hot tip device wherein optical diagnostic procedures can be performed through the heating element.

It is still another object of the present invention to provide a hot tip device having a filter glass heating element which absorbs a first range of wavelengths and passes a second range of wavelengths.

SUMMARY OF THE INVENTION

According to the present invention, these and other objects and advantages are achieved in a medical device for applying heat to a selected site in a lumen. The device comprises an elongated, flexible member having a proximal end and a distal end, a heating element attached to the distal end of the flexible member and optical fiber means extending through the flexible member. The heating element comprises optical filter means for absorbing a first range of wavelengths and for passing a second range of wavelengths. The optical fiber means has a distal end optically coupled to the heating element and has a proximal end adapted for receiving laser energy in the first range of wavelengths for heating the optical filter means and adapted for receiving laser energy in the second range of wavelengths for irradiating the lumen through the optical filter means.

In a preferred embodiment, the flexible member is a steerable guidewire including an elongated shaft having a distal end and a proximal end, and a tip attached to the distal end of the shaft. The shaft is sufficiently torsionally rigid along its length for controllably transmitting to the distal end substantially all of the rotation applied to the proximal end. The tip is adapted to be bent to a desired curve and is sufficiently flexible so as to adapt to and follow the contours of a blood vessel. The tip typically comprises a helically-wound spring, and the shaft comprises a flexible tube having a lumen therethrough and a core wire extending through the lumen in the tube. The optical fiber means is preferably an optical fiber located between the flexible tube and the core wire.

The optical filter means preferably comprises a smoothly curved body of filter glass located at the distal end of the helically-wound spring and affixed to the optical fiber. Preferably, the first range of wavelengths used to energize the heating element is in the near infrared band at or above about 800 nanometers. The second range of wavelengths is preferably in the ultraviolet or blue-green range of wavelengths and is used to stimulate fluorescence from tissue in the selected site of the lumen. The outside diameter of the shaft, the tip and the heating element preferably does not exceed about 0.020-inch.

According to another aspect of the present invention, there is provided a method for applying heat and laser radiation to a selected site in a body lumen. The method comprises the steps of advancing an elongated, flexible member through the lumen to the selected site, the flexible member having an optical fiber that extends therethrough and is terminated in an optical filter glass heating element, the filter glass heating element having an optical characteristic selected to absorb a first range of wavelengths and to pass a second range of wavelengths, directing laser radiation in the first wavelength range through the optical fiber for energizing the filter glass heating element in a heating mode, and directing laser radiation in the second wavelength range through the optical fiber so that the laser energy in the second wavelength range passes through the filter glass heating element and irradiates the selected site in a diagnostic mode.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
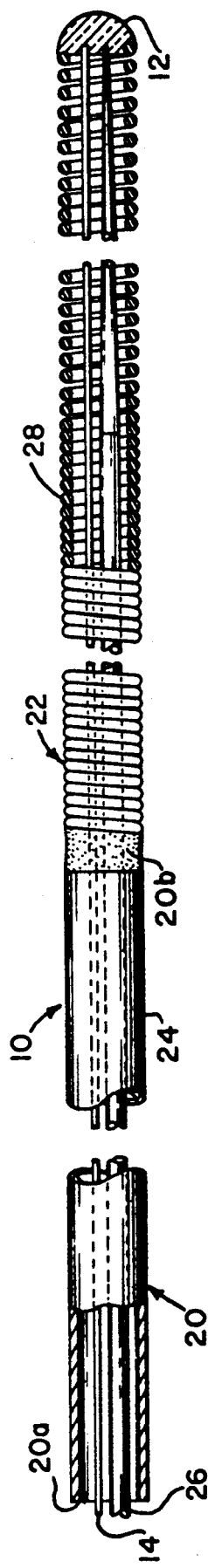
FIG. 1 illustrates a hot tip device in accordance with the present invention.
Figure 2:
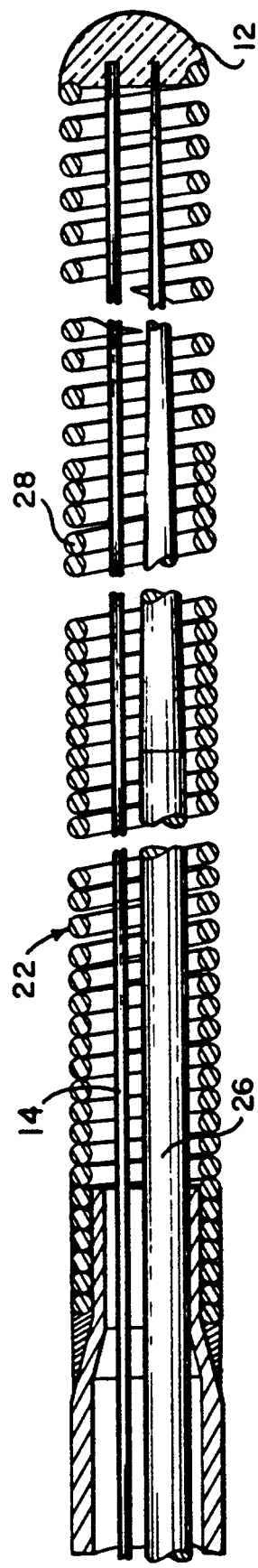
FIG. 2 is an enlarged cross sectional view of the distal end of the hot tip device of FIG. 1.

A hot tip device in accordance with the present invention is shown in FIGS. 1 and 2. The device generally includes an elongated, flexible member 10 having a sufficiently small diameter and sufficient flexibility to be advanced through a blood vessel to the coronary region. An optical filter heating element 12 is affixed to the distal end of flexible member 10. An optical fiber 14 extends through flexible member 10 and is optically coupled to heating element 12.

The filter glass heating element 12 has an optical transmission characteristic which absorbs a high percentage of optical energy in a first wavelength range and which passes a high percentage of optical energy in a second wavelength range. Thus, optical energy in the first wavelength range can be used to heat element 12, while optical energy in the second wavelength range passes through the filter glass heating element 12 and irradiates the adjacent portion of the blood vessel or stenotic deposits in the blood vessel. Element 12 is heated in order to melt and plow through plaque deposits.

Optical energy that passes through heating element 12 is preferably utilized to stimulate fluorescence from the tissue of the blood vessel. The fluorescence can be analyzed to distinguish between artherosclerotic tissue and normal tissue as described hereinafter.

Although the diagnostic feature of the hot tip device of the present invention is preferably used for sensing fluorescence from plaque or normal tissue, the laser energy that passes through the filter glass heating element can be used for any desired purpose, including viewing, illumination, heating, vaporization or thermography. By providing diagnostic capabilities, the reliability and control of the hot tip angioplasty procedure is improved.

In the embodiment of FIGS. 1 and 2, the flexible member 10 is a steerable guidewire that can be controllably advanced through an artery to the coronary region. The guidewire includes a shaft 20 having a proximal end 20a and a distal end 20b, and a tip 22 attached to the distal end of shaft 20. Shaft 20 includes an elongated, flexible tube 24, typically stainless steel, having a lumen therethrough. A core wire 26 extends through the lumen in tube 24. The shaft 20 is sufficiently torsionally rigid along its length for controllably transmitting to the distal end substantially all of the rotation applied to the proximal end.

The tip 22 includes a helically wound spring 28 attached to the distal end of flexible tube 24 and preferably having the same outside diameter as flexible tube 24. Core wire 26 includes a tapered tip portion which extends from flexible tube 24 through at least a portion of spring 28. The tip 22 is sufficiently flexible so as to adapt to and follow the contours of a blood vessel. The diameter of the steerable guidewire preferably does not exceed about 0.020-inch. Further details regarding the construction of a steerable guidewire are provided in the aforementioned U.S. Pat. No. 4,545,390, which is hereby incorporated by reference.

The filter glass heating element 12 is located at the distal end of spring 28 and is typically smoothly curved or rounded to reduce the possibility of perforating the wall of a blood vessel. The heating element 12 can be the same outside diameter as the remainder of flexible member 10 or can be larger in diameter than flexible member 10. Preferably, the filter glass heating element 12 is bonded directly to the distal end of optical fiber 14 by heating these elements and thereby creating a glass-to-glass connection. In the embodiment of FIGS. 1 and 2, the core wire 26 extends into and is mechanically coupled to heating element 12 to assist in retaining heating element 12 in position. Alternatively, core wire 26 can be terminated proximally of heating element 12.

The optical characteristics of filter glass heating element 12 are selected to absorb a first wavelength or range of wavelengths to cause heating of the filter glass and to pass a second wavelength or range of wavelengths for diagnostic purposes. It will be understood that the first and second wavelength ranges can be selected for a particular application. Generally, wavelengths in the infrared band produce efficient heating of element 12, while wavelengths in the ultraviolet and blue-green bands are desired for analysis of fluorescence from plaque deposits. Filter glass having a variety of different transmission characteristics can readily be obtained. The optical path from the distal end of optical fiber 15 through filter glass heating element 12 can range from a few micrometers to a few millimeters depending on the amount of attenuation that is acceptable in the pass band.

Figure 3:
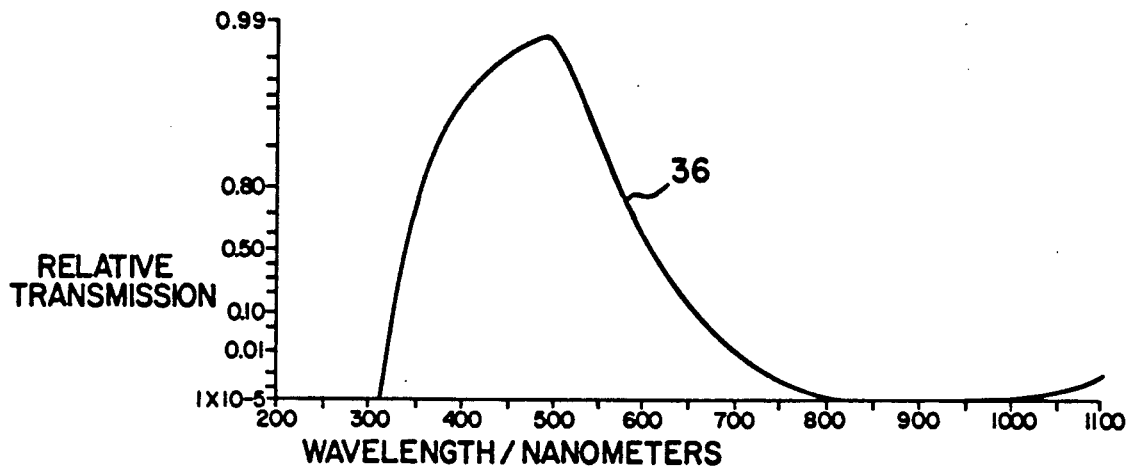
FIG. 3 is a plot of the transmission characteristic of the filter glass heating element.

In a preferred embodiment, the flexible tube 24 is a stainless steel hypotube having an outside diameter of 0.018-inch and an inside diameter of about 0.010-inch. The core wire 26 is stainless steel and has an outside diameter of 0.007-inch. The optical fiber 14 is a single mode optical fiber having an outside diameter of 150 micrometers, a core diameter of 100 micrometers, and a cladding diameter of 125 micrometers. The spring 28 is fabricated from 0.002-inch diameter platinum wire, with the spring coils preferably having the same outside diameter as flexible tube 24. In the present example, the filter glass heating element 12 is a type BG 39 available from Schott Fiber Optic of Duryea, Penn. The specified filter glass has a transmission bandwidth between about 325 and 610 nanometers. A typical transmission characteristic for filter glass heating element 12 is shown in FIG. 3 as curve 36, which shows relative transmission as a function of wavelength in nanometers.

In a preferred embodiment, the heating element 12 is heated by laser radiation at about 800 nanometers from a diode laser. A laser power level of about one watt is sufficient to heat element 12. A diode laser provides the advantages of small size, high reliability and low cost. Alternatively, other types of laser can be used to energize heating element 12.

The hot tip device of the present invention has been described in connection with a steerable guidewire. It will be understood that the filter glass heating element can be utilized at the distal end of a catheter as well as a steerable guidewire. Various techniques for mounting a heating element at the distal end of a catheter are disclosed in the aforementioned U.S. Pat. No. 4,773,413, which is hereby incorporated by reference. As indicated above, the primary requirements of the invention are to provide a filter glass heating element at the distal end of an elongated, flexible member 10 and to transmit optical energy through an optical fiber to the heating element.

Figure 4:
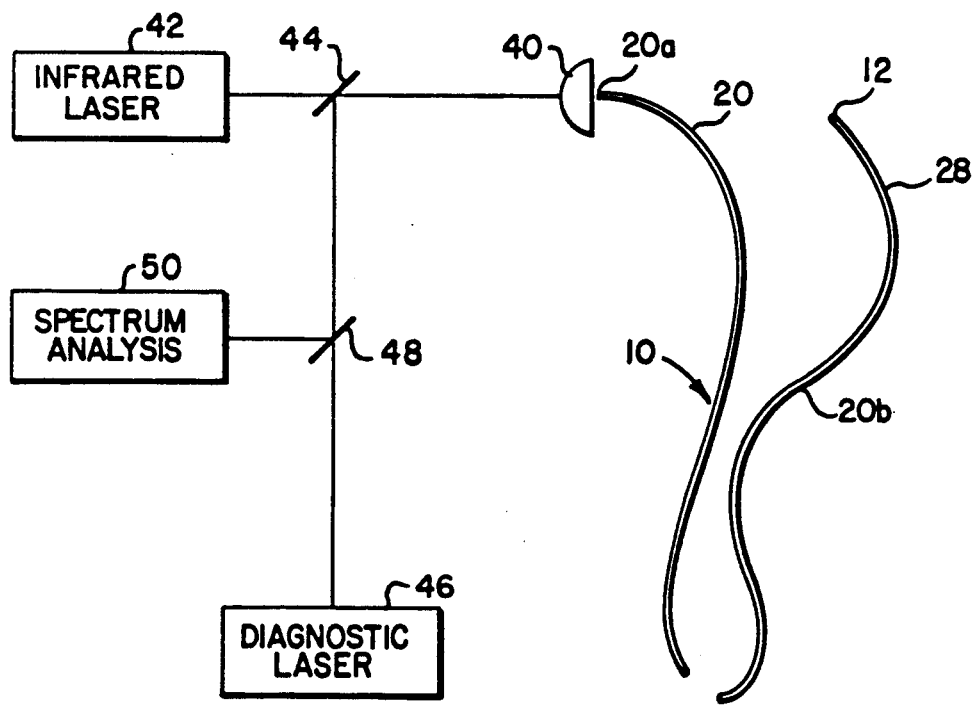
FIG. 4 is a block diagram of a system for utilizing the hot tip device of the present invention.

A block diagram of a system for operation of the hot tip device of the present invention is shown in FIG. 4. Optical energy is coupled to and from the optical fiber in the hot tip device through a lens 40. Laser energy from an infrared laser 42 is directed through a beam splitter 44 to lens 40. The infrared laser 42 can be a diode laser having an output at 800 nanometers. The beam splitter 44 includes an optical filter which transmits infrared radiation and reflects visible and ultraviolet radiation. The infrared laser 42 is energized during a heating mode to heat element 12. During the heating mode, the hot tip device is moved through the blood vessel to melt and plow through stenotic deposits.

A diagnostic laser 46 has an output directed through a beam splitter 48 to beam splitter 44. Diagnostic laser 46 typically has an output in the ultraviolet or blue-green range of wavelengths. An argon laser can be used to provide laser radiation in the blue-green range of wavelengths, while an excimer laser can be used to provide laser radiation in the ultraviolet range of wavelengths. In the present example, laser 48 produces ultraviolet radiation and the beam splitter 48 includes an optical filter which transmits ultraviolet wavelengths and reflects visible wavelengths. The output of the diagnostic laser 46 passes through beam splitter 48 and is reflected by beam splitter 44 into the hot tip device. The ultraviolet radiation passes through the optical fiber and through heating element 12 to irradiate a portion of the blood vessel distally of the heating element 12.

When stimulated by ultraviolet radiation, the tissue emits fluorescence in the visible range which passes through heating element 12 and through the optical fiber to the proximal end of the hot tip device. The fluorescence from the tissue is reflected by beam splitters 44 and 48 to a spectrum analysis unit 50. The spectrum of the fluorescence is analyzed to distinguish between normal and artherosclerotic tissue as described in the aforementioned patent number 4,785,806, which is hereby incorporated by references. In particular, the fluorescence intensity at wavelengths of 448, 514 and 538 nanometers can be analyzed to distinguish between plaque and normal tissue. The diagnostic laser 46 and the spectrum analysis unit 50 are utilized in a diagnostic mode. It will be understood that different diagnostic laser wavelengths can be utilized, depending on the diagnostic procedure.

While there have been shown and described what are present considered the preferred embodiments of the invention, it will be obvious to those skilled in the art that various changes and modifications may be made therein without departing from the scope of the invention as defined by the appended claims.

What is claimed is:

1. A medical device for applying heat to a selected site in a lumen, comprising:
   an elongated, flexible member having a proximal end and a distal end;
   a heating element attached to the distal end of said flexible member, said heating element comprising optical filter means for absorbing a first range of wavelengths and for passing a second range of wavelengths; and
   optical fiber means for transmitting both said first and said second ranges of wavelengths extending through said flexible member, said optical fiber means having a distal end optically coupled to said heating element and having a proximal end adapted for receiving laser energy in said first range of wavelengths for heating said optical filter means and adapted for receiving laser energy in said second range of wavelengths for irradiating said lumen through said optical filter means.

2. A medical device as defined in claim 1 wherein said optical filter means comprises a body of filter glass affixed to the distal end of said elongated flexible member.

3. A medical device as defined in claim 2 wherein said first range of wavelength is in the near infrared band and said second range of wavelengths is in the ultraviolet and blue-green bands.

4. A medical device as defined in claim 2 wherein said filter glass is selected to absorb laser radiation at about 800 nanometers and to pass laser radiation in a range of about 325 to 610 nanometers.

5. A medical device as defined in claim 1 wherein said flexible member comprises
   an elongated shaft having a distal end and a proximal end, said shaft being sufficiently torsionally rigid along its length for controllably transmitting to the distal end substantially all of the rotation applied to the proximal end, and
   a tip attached to the distal end of said shaft, said tip being sufficiently flexible so as to adapt to and follow the contours of a blood vessel.

6. A medical device as defined in claim 5 wherein said shaft, said tip and said heating element have a diameter that does not exceed about 0.020-inch.

7. A medical device as defined in claim 5 wherein said tip comprises a helically-wound spring.

8. A medical device as defined in claim 7 wherein said shaft comprises a flexible tube having a lumen therethrough and a core wire extending through the lumen in said tube.

9. A medical device as defined in claim 8 wherein said tip further includes a tapered distal region of said core wire extending beyond the distal end of said tube and passing through at least a portion of said helically-wound spring.

10. A medical device as defined in claim 9 wherein said optical fiber means comprises an optical fiber passing through said shaft between said core wire and said tube.

11. A medical device as defined in claim 10 wherein said optical fiber passes through said tip between the tapered distal region of said core wire and said helically-wound spring.

12. A medical device as defined in claim 10 wherein said optical fiber means comprises a smoothly curved body of filter glass located at the distal end of said helically-wound spring and affixed to said optical fiber.

13. A medical device for applying heat and laser radiation to a selected site in a lumen, comprising:
an elongated, flexible member having a proximal end and a distal end;
an optical filter glass element attached to the distal end of said flexible member for absorbing a first range of wavelengths and for passing a second range of wavelengths;
optical fiber means extending through said flexible member, said optical fiber means having a distal end optically coupled to said filter glass element;
means for coupling laser radiation in said first range of wavelengths through said optical fiber means for heating said filter glass element in a heating mode; and
means for coupling laser radiation in said second range of wavelengths through said optical fiber means for irradiating said lumen through said filter glass element in a diagnostic mode.

14. A medical device as defined in claim 13 wherein said optical filter means comprises a body of filter glass affixed to the distal end of said elongated flexible member.

15. A medical device as defined in claim 14 wherein said first range of wavelengths is in the near infrared band and said second range of wavelengths is in the ultraviolet and blue-green bands.

16. A medical device as defined in claim 14 wherein said filter glass is selected to absorb laser radiation at about 800 nanometers and to pass laser radiation in a range of about 325 to 610 nanometers.

17. A medical device as defined in claim 13 wherein said flexible member comprises
an elongated shaft having a distal end and a proximal end, said shaft being sufficiently torsionally rigid along its length for controllably transmitting to the distal end substantially all of the rotation applied to the proximal end, and
a tip attached to the distal end of said shaft, said tip being sufficiently flexible so as to adapt to and follow the contours of a blood vessel.

18. A medical device as defined in claim 17 wherein said shaft, said tip and said heating element have a diameter that does not exceed about 0.020-inch.

19. A medical device as defined in claim 17 wherein said tip comprises a helically-wound spring.

20. A medical devices as defined in claim 19 wherein said shaft comprises a flexible tube having a lumen therethrough and a core wire extending through the lumen in said tube.

21. A medical device as defined in claim 20 wherein said tip further includes a tapered distal region of said core wire extending beyond the distal end of said tube and passing through at least a portion of said helically-wound spring.

22. A medical device as defined in claim 21 wherein said optical fiber means comprises an optical fiber passing through said shaft between said core wire and said tube.

23. A medical device as defined in claim 22 wherein said optical fiber passes through said tip between the tapered distal region of said core wire and said helically-wound spring.

24. A medical device as defined in claim 22 wherein said optical fiber means comprises a smoothly curved body of filter glass located at the distal end of said helically-wound spring and affixed to said optical fiber.

25. A method for applying heat and laser radiation to a selected site in a body lumen, comprising the steps of:
advancing an elongated, flexible member through the lumen to the selected site, said flexible member having an optical fiber that extends therethrough and is terminated in an optical filter glass heating element, said filter glass heating element having an optical characteristic selected to absorb a first range of wavelengths and to pass a second range of wavelengths;
directing laser radiation in said first wavelength range through said optical fiber for heating of said heating element in a heating mode; and
directing laser radiation in said second wavelength range through said optical fiber so that the laser energy in said second wavelength range passes through said filter glass heating element and irradiates the selected site in a diagnostic mode.

26. A method for applying heat and laser radiation as defined in claim 25 wherein the step of advancing an elongated, flexible member through the lumen includes advancing the flexible member through a blood vessel to a stenosed site.

27. A method for applying heat and laser radiation as defined in claim 26 where in the step of directing laser radiation in said second wavelength range includes directing ultraviolet radiation through said optical fiber and said filter glass heating element to cause fluorescence by the stenosed site.

* * * * *